United States Patent [19] [11] Patent Number: 4,843,147
Levy et al. [45] Date of Patent: Jun. 27, 1989

[54] ANHYDROUS ENHANCED COUPLING OF PROTEINS

[75] Inventors: Julia G. Levy; Daniel Liu, both of Vancouver B. C., Canada

[73] Assignee: University of British Columbia, Vancouver, Canada

[21] Appl. No.: 248,267

[22] Filed: Sep. 21, 1988

Related U.S. Application Data

[63] Continuation of Ser. No. 927,847, Nov. 6, 1986, abandoned.

[51] Int. Cl.$^4$ .......................... C07K 3/08; C07K 17/06; A61K 39/395
[52] U.S. Cl. ..................................... 530/391; 530/389; 530/387; 530/405; 530/409; 530/807; 424/85.8; 436/823
[58] Field of Search ............... 530/391, 387, 388, 389, 530/405, 409, 807; 424/85; 436/863

[56] References Cited

U.S. PATENT DOCUMENTS 4,363,758  12/1982  Masuho et al. ...................... 530/391
4,487,714  12/1984  Kato et al. ........................... 530/391
4,629,691  12/1986  Collins et al. ....................... 530/387

OTHER PUBLICATIONS

Pimm et al., Chem Abs., 105(11): 93642k, 1986 (for IRCS Med Sci. 14(2), 104–105).
Streitweiser and Heathcock, "Introduction to Organic Chemistry," p. 167, 2nd Edition, 1985.
Bauminger et al., Methods in Enzymology, pp. 151–159, 70, 1980.
Mastrioanni et al., J. Phys. Chem., 76(21), 3050–3057, 1972.
Atassi et al., Bioch. Biophys. Acta., 670, 300–302, (1981).

Primary Examiner—Margaret Moskowitz
Assistant Examiner—Jeff P. Kushan
Attorney, Agent, or Firm—Irell & Manella

[57] ABSTRACT

An improvement in a method to conjugate a protein which must resist denaturation with a variable component using a carbodiimide condensing agent utilizes a polar aprotic solvent as the medium for condensation. This improvement results in shorter reaction times and improved coupling efficiency.

12 Claims, No Drawings

4,843,147

ANHYDROUS ENHANCED COUPLING OF PROTEINS

TECHNICAL FIELD

The invention relates to conjugating biologically active molecules, in particular, to conjugating proteins. More specifically, it relates to conducting conjugation reactions in nonaqueous solvents and thereby enhancing the effectiveness of coupling.

BACKGROUND ART

Within the last decade it has become apparent that advantages are available from utilizing the specific interaction of the antibodies produced by the immune system or fragments thereof to confer a homing capability on a substance to be delivered to a particular target location in a subject. A common application is the use of immunotoxins which are conjugates between toxic materials, such as ricin or abrin, with an antibody preparation that is specific for a tissue against which the toxin is expected to react. Other examples include the conjugation of organic labels, such as fluorescent labels, to immunoglobulins in order to identify the location of certain target tissues.

Analogous conjugates have also been formed to confer immunogenicity on materials carrying epitopes to which antibodies are to be raised, but which lack sufficient size to be immunogenic. For example, a substantial amount of research has been done on the preparation of peptide vaccines by ligating short amino acid sequences to carrier proteins. This permits the relevant epitope to be used in quantity and to be synthesized chemically.

In each of these instances, it is necessary to find an efficient and nondestructive way to couple a protein subject to denaturation, i.e., the homing agent or carrier protein, with an "active" substance of interest. Conditions must be found which provide satisfactory amounts of product while maintaining the conformation of the protein.

Two basic approaches have been taken. The first uses linkers which become part of the conjugate. These linkers are homobifunctional or heterobifunctional, and include those capable of forming, for example, disulfide linkages through the thiol groups of cysteine moieties in the substrate proteins, or of the formation of amide linkages between N-terminal amino group or the amino side chains or lysine residues and activated acyl moieties such as succinimidyl esters. In general, this approach involves highly reactive functional groups on the linker and is reasonably facile with respect to the substrates for conjugation. However it is often useful to employ functional groups which may be less reactive, such as those capable of hydrazone formation.

A second approach, particularly useful in conjugating two protein moieties, uses a dehydrating agent such as a carbodiimide to effect the formation of, for example, new peptide bonds by reaction of a carboxyl moiety on one member of the conjugate with a free amino group on the other. In this case, the reagent does not become part of the conjugate. This reaction is not particularly facile since the carboxyl group is not activated; the carbodiimide provides the active intermediate and shifts the equilibrium by removing the elements of water to form the peptide bond.

Both approaches to conjugation have generally been conducted in aqueous solvents because the protein material forming the conjugate is easily denatured. Proteins are designed to be stable in an aqueous environment and are known to denature even in solvents, such as ethanol, which would be thought to be reasonably analogous to an aqueous medium. Also, protein conjugate components tend to be relatively insoluble in nonaqueous solvents.

Effecting a conjugation between proteins using functionalities which result in the elimination of water, i.e., dehydration, is therefore often done in aqueous medium. While workable, this clearly is not particularly facile nor efficient. Since relatively long reaction times are required, the opportunity for side reactions is also great.

It has previously been disclosed that polar aprotic solvents may be present in the reaction mixture without resulting in sufficient denaturation of product to undermine its utility. For example, in the conjugation procedure described in Mew. D., et al. *J. Immunol* (1983) 130: 1473–1477, hematoporphyrin is conjugated to antibody protein after an initial reaction with 1-ethyl-3-(3-dimethylaminopropyl)-carbodiimide HCl (EDCI) using a total volume of approximately 2.5 ml of which 0.8 ml is dimethyl formamide (DMF). However, applicants are aware of no instance in which the conjugation has been successfully conducted in what amounts to a completely nonaqueous environment. The present invention demonstrates that such a reaction medium is not only nondenaturing during the course of the reaction, but is also advantageous in increasing the rate of reaction and the efficiency of coupling.

DISCLOSURE OF THE INVENTION

The invention provides a method of linking biologically active moieties without denaturation using a nonaqueous reaction medium in the presence of a conjugation reagent. The nonaqueous medium comprises a polar aprotic solvent, and at least one of the components of the conjugate is a biologically functional protein, typically, for example, an immunoglobulin. The other components may also be a protein, or any of a variety of useful compounds.

Thus in one aspect the invention relates to a method of conjugating biologically functional materials in the presence of a conjugation reagent wherein the method is enhanced and improved by conducting the conjugation in a nonaqueous medium. In other aspects, the invention relates to a composition of matter comprising at least the two components to be conjugated, a conjugation reagent, and a nonaqueous solvent.

MODES OF CARRYING OUT THE INVENTION

The invention concerns a specific improvement in a method of conjugating materials capable of linkage by virtue of formation of a peptide bond, ester linkage, hydrazone formation, acetal formation, or other specific linkage which is the result of a condensation reaction, involving the elimination of water. The "dehydration" generally can be made to occur, though relatively slowly, in the aqueous solution thought to be required to maintain the conformation of a protein component.

CONJUGATION REAGENTS

The condensation is brought about by a "conjugation reagent" which term is used herein to include any reagent which, as at least a part of its function, results in the elimination of water to form a new covalent bond between compounds and which reaction results in the conjugation of two desired members of a resulting conjugate. Specifically, "conjugation reagent" includes both "dehydrating agents" and "linking reagent".

A "dehydrating agent" is herein defined as a material, such as carbodiimide, which does not itself become part of the conjugate but is responsible for the elimination of water to form a new bond between the two components of the conjugate. There are a series of carbodiimides substituted with various organic moieties. The basic carbodiimide structure is —N═C═N wherein each N is optionally substituted by an organic moiety. This functional group functions stoichiometrically to remove water by conversion to the corresponding urea of the formula —NHCONH—. Typical carbodiimides useful in the improved process of the reaction include diethyl carbodiimide, dicyclohexyl carbodiimide (DCC), and 1-ethyl-3-(3-dimethylaminopropyl) carbodiimide (EDCI).

On the other hand, "linking reagents" are reagents which themselves become part of the product conjugate and which contain functional groups capable of reacting with each component of the final products. These are commonly known as "linkers" or by the trademark "Double Agents". A variety of functional groups present on the linkers is employed for a range of applications, and a large number of such "linking agents" are commercially available. Some are quite simple in concept, such as the dialdehydes, in particular glutaraldehydes, in which two identical functional groups react similarly with target components. In the case of glutaraldehyde, for example, the two carbonyl groups react with amino side chains of proteins to form imine linkages that result when the elements of water are removed from the new C—N bond. Other linkers are extremely sophisticated, such as, for example, those containing activated esters and reactive sulfhydryl groups. In order to be defined as "linking agents" within the scope of the invention. However, at least one of the two functional groups must link to the component by virtue of a reaction in which water is eliminated. Glutaraldehyde, of course, falls in this category.

However, for heterobifunctional linking agents, it is only necessary that one of the two functional groups react by dehydration. Thus, included within the invention are conjugation reactions involving heterobifunctional linking agents in which one functional group forms another type of linkage, such as disulfide which does not involve a dehydration. The other functional group must, however, involve the elimination of water, such as the reaction of a "hydrazine-type" functional group with the carbonyl moiety of a glycoprotein sugar to obtain the hydrazone. By "hydrazine-type" functional group is meant any of those reagents which react with carbonyl functions in a manner analogous to that of hydrazine including the organic hydrazines of the formula R—NHNH$_2$, and the organic semicarbazides which contain the functional group NHCONHNH$_2$. There are a number of such configurations known in the art which are applicable.

In addition, of course, the linking agent may form its bond with one of the components by virtue of a reaction effected by a dehydrating agent. Thus, the linking agent may contain as one or more functional groups a simple amine or carboxyl group which then can be induced to form a peptide bond with a peptide component through the mediation of another reagent such as a carbodiimide to remove water. Also employable are linkages between a carbonyl or alcohol group on the linker mediated by a dehydrating agent to obtain an acetal with an alcohol or carbonyl counterpart of the component.

THE COMPONENTS

A. Preservable Proteins

All of the conjugates formed by the method of the invention involve a protein that must not undergo denaturation in the process, i.e., a "preservable protein". By "preservable" protein component is meant a protein which becomes a member of the conjugate without sufficient conformational change to be denaturated or to destroy its capability to function.

At least one component of the conjugate is such a protein. Most commonly this is an immunoglobulin or an immunologically reactive fragment thereof, such as an Fab, Fab' or an F(ab)$_2$ fragment. These immunospecific proteins are useful in conferring on the conjugate the ability to bind specifically to a desired target tissue or specific reactivity in assay systems. Thus, materials toxic to tumors, for example, have been linked to immunoglobulin moieties specific for particular types of tumor tissue which as the carcinomas exhibiting CEA antigens or the various anti-breast tumor monoclonal antibodies available. A large number of monoclonals specific for lymphoid tissue useful in treating leukemia with conjugates of this type is found in a series of U.S. patents including U.S. Pat. Nos. 4,340,535; 4,363,799; and 4,361,549. A number of similar antibodies are commercially available including T101, UCHT1, and TA1. Of course, a wide variety of antibodies, monoclonal or polyclonal, is available for use in immunoassays, and such antibodies are bound to labeling groups such as fluorescent, radioactive, or enzymic labels; by the method of the invention.

Another commonly encountered "preservable" protein component is a "carrier" protein—a relatively antigenically neutral protein such as bovine serum albumin (BSA) or keyhole limpet hemacyanin (KLH) which is linked to a smaller, typically antigenic, peptide, often synthetic, in order to confer immunogenicity on the desired antigen. Considerable effort has been made to deduce the portions of viral associated proteins, for example, which are responsible for recognition of neutralizing antibodies, and using such smaller regions as the antigenic component of vaccines. These epitopes are typically only 8–10 amino acids in length, and administered alone would be ineffective in stimulating the formation of antibodies. They are therefore conjugated to the above-mentioned carrier proteins in order to render them immunogenic. The same general approach is used to confer immunogenicity on smaller nonpeptide molecules such as drugs or steroid hormones by conjugation to a larger carrier protein.

The above-mentioned examples of conjugation thus involve, as one member of the conjugate pair, a protein material which needs, in order to fulfill its function, to resist denaturation in the conjugation process. The antibody must retain its ability to recognize the target tissue; the carrier protein must not denature to assume conformations which destroy its antigenically neutral character. Other instances in which a protein component serves a function which requires that it retain substantially its original conformation are less common, but are included within the scope of the invention, as the foregoing illustrations are meant simply to clarify the nature of the invention and are not intended to be limiting.

It should be noted that the proteins which form members of the conjugate may often be, and indeed are in the case of immunoglobulins, glycoproteins containing substantial percentages of saccharide moieties. This is significant in that the saccharide moieties may also be used for providing the functional group participating in conjugation and, by virtue of their ability to form hydrazone-type condensations and acetals, are capable of specific linkages whose formation is effected by the elimination of water.

B. Variable Components

The other member of the conjugate may be of considerable variety, including the peptide and polypeptide vaccine components and toxins mentioned above; it is referred to herein as a "variable" component. Also useful as the second member of the conjugate are various pharmaceuticals such as adriamycin, hematoporphyrin, steroid hormones such as androsterone and estradiol, relatively simple molecules such as indomethacin, naproxen, nicardopine, diazepam, and the like; vitamins such as vitamin D, vitamin A, and pyridoxal; or labeling compounds such as fluorescein, dansyl, or rhodamine groups, or complexes containing radioactive isotopes.

It is, of course, apparent that the variable component can itself be a preservable protein. Indeed, a number of the toxins used in immunotoxin constructs are glycoproteins such as ricin, ricin A, abrin, gelonin, or diphtheria or other bacterial toxins. In addition, the variable component may have enzymic activity and be targeted to a particular tissue, or may be a label for an enzyme mediated immunoassay. Such enzymes include urokinase, tissue plasminogen activator, alcohol dehydrogenase, peroxidase, catalase, and various esterases may have both therapeutic and diagnostic uses.

The protein component which serves as the variable component may also be a hormone or growth factor such as growth hormones, tumor angiogenesis factor, epidermal growth factor, nerve growth factor and smaller proteins such as hormone releasing hormones including corticotropin releasing factor, leutinizing hormone releasing hormone, and so forth. The protein may have certain regulatory capabilities such as calcitonin, vasopressin, renin, or the atrial peptides. Various other proteins, such as antiviral agents, including $\alpha$-, $\beta$-, and $\gamma$-interferon; antimicrobial peptides; lymphokines such as the various colony-stimulating factors, interleukins, and lymphotoxin, etc., may also be used.

The terms "protein" and "peptide" are used as distinct terms herein as the size of the molecule effects its tendency to denature. Thus, "protein" is given its typical definition of an amino acid sequence (with or without accompanying glycosylation or other post-translational modification) of more than 50 amino acids; peptides are similarly defined except that the amino acid sequence is 50 amino acids or less. While the borderline is arbitrary, the intent is clear. Typical peptides designed to constitute epitope regions of larger proteins are frequently only 8–10 amino acids in length while most enzymes are of the order of 100 amino acids or more. Most hormones contain more than 50 amino acids, although in this category, the division into "proteins" and "peptides" among the group is not so clear.

Additional variable components include a variety of pharmaceutically useful agents such as epinephrine, streptomycin, kanamycin or other antibiotics, anti-inflammatory agents such as dexamethazone, anti-tumor agents such as 5-fluorouracil and methotrexate and antihistamines such as diphenylhydramine.

The foregoing list is, of course, vastly incomplete as would be any list of reasonable length. Any moiety which contains, or which can be modified to contain, a functional group capable of covalent bonding with a corresponding functional group in the protein component by virtue of a dehydration reaction or can be bound to a functional group of a linking agent can be used in the method of the invention.

FORMATION OF THE CONJUGATE

The conjugation reaction or reactions is or are carried out in a nonaqueous solvent. The nonaqueous solvent is characterized as a polar aprotic solvent. The polarity need not be great, as methylene dichloride is included as a workable solvent, although the hydrocarbons and carbon tetrachloride are not. Such solvents include, for example, dimethyl sulfoxide (DMSO), tetrahydrofuran (THF), N,N-dimethylformamide (DMF); 1,2-dimethoxyethane ((DME); hexamethyl phosphoric triamide (HMPA); acetonitrile, acetone, ethyl acetate, the glymes, such as dimethoxyethane, and methylene dichloride. Again, this list is representative, not all inclusive. Any aprotic solvent which is not completely nonpolar will do. It also may not be necessary that both components be completely dissolved in the solvent; "dispersed" or "dispersion" is used herein to denote partial or complete solution.

According to the method of the invention the conjugation reagent and the components of the reaction are placed in a nonaqueous solvent either by mixing them into the solvent together or sequentially and the reaction time is extended as needed to effect coupling. Typically reaction time are less than a half hour regardless of specific protocol and may be as little as a few minutes. The temperature of the reaction is typically room temperature although slightly lower or higher temperatures may also be used, depending on the particular solvent. The reagents are used at a concentration of 1–10 mg of each component per ml in a typical reaction, although these limits, too, are not absolutely definite and are subject to considerable variation depending on the molecular weights of the reagents as would generally be understood by practitioners.

The protocol by which the reaction is conducted depends, of course, on the nature of the conjugating agent and on the nature of the components. In its simplest embodiment, the components and the coupling agent may simply be mixed together in the presence of the nonaqueous solvent and allowed to react. However, it may be preferable to permit the variable component to react first with the conjugating agent, especially if the variable component is not subject to denaturation, and then to add the preservable protein component. The following are various suggested protocols.

In one approach, the variable component is mixed with a linking agent which contains a functional group capable of reacting with the variable component through dehydration mediated by a dehydrating agent such as a carbodiimide. The variable component, linking agent, and dehydrating agent are mixed in the nonaqueous solvent and stirred until reaction is substantially complete. The perservable protein component, which is capable of reacting with the other functional group of the linking agent without the benefit of a dehydrating agent, such as a reactive thiol functional group, is then added, and the second phase of the coupling completed.

Alternatively, a variable component which reacts directly with one of the functional groups on a linking agent may be used. In this situation, the linking agent and the variable component are mixed in the nonaqueous solvent and permitted to react, whereupon the preservable protein component is added. If the remaining functional group on the linker requires the presence of a dehydrating agent in order to effect reaction with the preservable protein, the dehydrating agent is added either simultaneously with the preservable protein, or previous to it to undergo preliminary reaction with the linker, now attached to the variable component.

While the above protocols are preferred, it is within the scope of the reaction to react the preservable protein component with the linking agent or with a dehydrating agent as a first step, and to add the variable component second. The order is of course relatively inconsequential when the variable component is itself a preservable protein. However, the relative stabilities of the two proteins to denaturation in the particular solvent may determine the more convenient choice of protocol.

In a preferred protocol, using direct action of a dehydrating agent on the two components to effect conjugation, the variable component is mixed first with the dehydrating agent in a nonaqueous solvent and incubated for a short time, typically a few seconds to a few minutes up to about an hour, before addition of the antibody or other preservable protein preparation at a similar concentration in the same solvent.

It is also preferred that the reaction be conducted under an inert atmosphere such as helium or nitrogen, preferably nitrogen for convenience, although this, too, is not absolutely necessary.

Thus, in a typical protocol, 2 ml of a dispersion in DMSO containing 5 mg each of the variable component and the dehydrating agent is prepared and stirred for 30 minutes at room temperature under nitrogen. To this is added a dispersion containing 2 mg of a immunoglobulin in 2 ml of DMSO, and the resulting mixture stirred for another 10 minutes. This mixture is then worked up by dilution in phosphate-buffered saline, pH 7.4 (PBS) by adding 5 times the volume of PBS containing 50 $\mu$l monoethanolamine, and is then dialyzed against PBS using 3 changes of wash.

Alternatively, 2 ml of a dispersion containing 5 mg each of the variable component, a linking agent, and a dehydrating agent is prepared and stirred for approximately 15 minutes at room temperature under nitrogen. To this is then added a dispersion containing about 2 mg of a carrier protein in 2 ml of tetrahydrofuran and the resulting mixture stirred for another 10 minutes. The mixture is then worked up as described above.

EXAMPLES

The following examples are intended to illustrate but not to limit the invention.

EXAMPLE 1

Protocols for Conjugation of Hematoporphyrin with CAMAL-1

CAMAL-1 antibodies are specific to a leukemia associated antigen which is expressed in cells of a majority of patients with acute nonlymphocytic leukemia. CAMAL-1 represents a monoclonal antibody prepared as described by Shipman, R., et al, *Brit J Cancer* (1983) 47: 849-853. Hematoporphyrin is a well-known subtance and has received considerable attention because of the utility it and its simple derivative (HPD) exhibits in photochemically mediate treatment for cancers and certain skin diseases (see, for example, Dougherty, T. J., et al, *J Invest Dermatol* (1981) 77: 122-124; Dougherty, T. J., et al, *Cancer Res* (1979) 38: 2628-2635; Dougherty, T. J., et al, *J. Nat'l Cancer Inst* (1979) 62: 231-237. In the following protocols, CAMAL-1 antibodies and hematoporphyrin (Hp) are coupled using the coupling agent EDCI described above.

A. A dispersion of 5 mg hematoporphyrin plus 5 mg of EDCI in 2 ml spectral grade DMSO was stirred for 30 minutes under nitrogen at room temperature. A preparation containing 5 mg of lyophilized CAMAL-1 in 2 ml DMSO was then added and the resulting mixture stirred for one minute at room temperature, then diluted in 5 times PBS containing 50 $\mu$l monoethanolamine and dialyzed against PBS using 3 changes of counter-solvent. The resulting conjugate was recovered from the dialyzate and analyzed for the stoichiometry of Hp/CAMAL-1. The conjugate was shown to contain 280 $\mu$g Hp/mg CAMAL-1.

B. The protocol of paragraph A was repeated except that the final mixture after addition of CAMAL-1 was stirred for either 5 minutes or 10 minutes; the remainder of the procedure was identical. These additional action times resulted in stoichiometries of 1100 $\mu$g Hp/mg CAMAL-1 and 1200 $\mu$g Hp/mg CAMAL-1 respectively.

EXAMPLE 2

Coupling of Hematoporphyrin to Various Proteins

A. Peanut Agglutinin 4 mg of hematoporphyrin plus 4 mg of EDCI in 2 ml spectral grade DMSO were stirred under nitrogen for 30 minutes at room temperature. To the mixture was added 2.5 mg lyophilized peanut agglutinin (PNA) in 1 ml DMSO and the mixture stirred for an additional two minutes. The mixture was then taken up in PBS and dialyzed as described in Example 1 resulting in 50 $\mu$g hematoporphyrin per mg PNA.

B. B16G 11 mg of hematoporphyrin plus 11 mg EDCI in 4 ml spectral grade DMSO was stirred for 30 minutes under nitrogen at room temperature before the addition of 20 mg lyophilized B16G antibodies, prepared as described by Maier, T., et al, *J. Immunol* (1983) 131: 1843, in 2 ml DMSO. The resulting mixture was stirred for 40 seconds at room temperature and worked up as described above. The resulting product contained 375 $\mu$g Hp/mg B16G.

C. R-$\alpha$ MIg

400 $\mu$g of EDCI and 400 $\mu$g hematoporphyrin in 1 ml DMSO were stirred for 30 minutes under nitrogen at room temperature as above before the addition of 800 $\mu$g lyophilized R-$\alpha$ MIg antibodies, prepared as described by Mew, D., et al, *J Immunol* (1983) 1473-1477, in 1 ml DMSO. The resulting mixture was stirred for 30 seconds and worked up as described above to obtain a product containing 200 $\mu$g Hp/mg R-$\alpha$ MIg.

EXAMPLE 3

Additional Variable Components

A. 4 mg of the boron cage compound

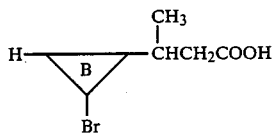

containing a free carboxyl group was mixed with 8 mg EDCI and 2 ml DMSO and incubated under nitrogen with stirring for 30 minutes at room temperature as above. To this mixture was added 10 mg lyophilized CAMAL-1 in 2 ml DMSO and the resulting mixture stirred for varying times, removing samples for work up and analysis as above described, except that 4 countersolvent change were used. The boron cage compound proved unstable, however.

B. A 15 mg sample of the tricyclic compound

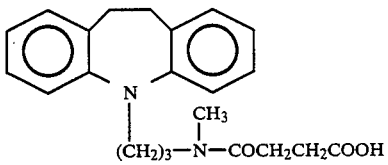

containing a free carboxyl group along with 15 mg EDCI is mixed in 2 ml spectral grade DMSO and stirred for 30 minutes under nitrogen at room temperature. To this mixture was added 13 mg of either BSA or KLH in 2 ml DMSO and the reaction mixture worked up as above.

C. A similar procedure was conducted using 5 mg CCK peptide with 5 mg EDCI and 5 mg BSA or KLH in 2 ml DMSO.

D. 50μ curies of $C^{14}$-labeled succinic acid (7 mg) with 7 mg EDCI were mixed in 2 ml DMSO incubated as above, and then supplemented with 10 μg BSA in 2 ml DMSO. The resulting mixture was stirred for various time periods and the reaction mixture worked up to test stoichiometry as described above. The results showed variable amounts of succinic acid per mg BSA as follows:

| Minutes | μcuries/mg |
|---------|-----------|
| 7.5     | 66        |
| 15      | 42        |
| 30      | 16        |
| 60      | 36        |
| 120     | 69        |
| 240     | 110       |
| 24 hrs  | 52        |

E. Similar procedures were conducted using 3-bromo-4-methylbenzoic acid and 2-bromophenylacetic acid as variable components.

F. Three mg of lyophilized R-α MIg were reacted in 2 ml DMSO with 150 μg alkaline phosphatase in the presence of 3 mg EDCI. The reaction was allowed to continue for 1 min and then neutralized in Tris-HCl buffer containing 0.11M sodium azide. The work-up was as above described, by dialyzing against BSA, and the conjugate was recovered by lyophilization of the dialyzate. Stoichiometry could not be determined, as the alkaline phosphatase was unstable to lyophilization.

We claim:

1. A method for conjugating an immunoglobulin or an immunologically reactive fragment thereof through an amide linkage with a variable component, said component having a functionality capable of forming an amide bond to the immunoglobulin or fragment by means of a dehydration reaction effected by a dehydrating agent, which method comprises
   mixing said immunoglobulin or fragment thereof with said variable component and dehydrating agent in a medium consisting essentially of an anhydrous polar aprotic solvent for a time up to about ten minutes.

2. The method of claim 1 wherein the solvent is DMSO.

3. The method of claim 1 wherein the dehydrating agent is a carbodiimide.

4. The method of claim 3 wherein the carbodiimide is ECDI.

5. The method of claim 1 wherein the variable component is a pharmaceutically active nonprotein compound.

6. The method of claim 5 wherein the pharmaceutically active nonprotein compound is hematoporphyrin.

7. The method of claim 1 which is conducted by mixing the dehydrating agent and variable component in a portion of said solvent, stirring, and then adding the immunoglobulin or fragment in additional solvent.

8. The method of claim 7 wherein the stirring is conducted under an inert atmosphere.

9. The method of claim 1 which is conducted by mixing the dehydrating agent and variable component in a portion of said solvent, stirring, and then adding the protein component in additional solvent,
   incubating for a time period of 40 seconds to one-half hour, and then diluting in aqueous medium.

10. The method of claim 9 wherein said incubating is ten minutes or less.

11. A reaction mixture which comprises an immunoglobulin or immunologically reactive fragment thereof, a variable component with a functionality capable of forming an amide bond to the immunoglobulin or fragment, a dehydrating agent, and medium consisting essentially of an anhydrous DMSO.

12. The reaction mixture of claim 11 wherein the variable component is hematoporphyrin.

* * * * *